(12) United States Patent
Abe et al.

(10) Patent No.: US 7,214,937 B2
(45) Date of Patent: May 8, 2007

(54) ELECTRON MICROSCOPE

(75) Inventors: Katsuaki Abe, Hitachinaka (JP);
Osamu Komuro, Hitachinaka (JP);
Kenichi Nishigata, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/052,809

(22) Filed: Feb. 9, 2005

(65) Prior Publication Data

US 2005/0145793 A1    Jul. 7, 2005

Related U.S. Application Data

(63) Continuation of application No. 09/811,719, filed on Mar. 19, 2001, now abandoned.

(30) Foreign Application Priority Data

Aug. 25, 2000 (JP) ............................. 2000-260877

(51) Int. Cl.
*H01J 37/153* (2006.01)
*G21K 7/00* (2006.01)
(52) U.S. Cl. ...................... 250/311; 250/306; 250/310; 250/492.2; 250/492.3
(58) Field of Classification Search ................ 250/310, 250/311, 307, 306
See application file for complete search history.

(56) References Cited

U.S. PATENT DOCUMENTS 6,259,660 B1    7/2001    Inokuchi
6,259,960 B1 *  7/2001    Inokuchi ..................... 700/110
6,334,097 B1 * 12/2001    Yoshitake et al. .......... 702/185
6,404,911 B2    6/2002    Ishihara et al.
6,476,388 B1 * 11/2002    Nakagaki et al. ........... 250/310
6,476,913 B1 * 11/2002    Machida et al. ............ 356/394
6,542,830 B1 *  4/2003    Mizuno et al. ............... 702/35
6,549,222 B1    4/2003    Skoll

FOREIGN PATENT DOCUMENTS

JP    A 64-84555    3/1989
JP    A 6-310072    11/1994

* cited by examiner

*Primary Examiner*—Nikita Wells
(74) *Attorney, Agent, or Firm*—Kenyon & Kenyon LLP (57) ABSTRACT

In order to provide an electron microscope which enables the operator to position the field-of-view easily and accurately on a target fault, the electron microscope for observing a surface or inside of a semiconductor wafer or a mask for exposing a semiconductor pattern for faults and/or foreign objects, is provided comprising a function of loading measurement data of coordinates or sizes of faults or objects which were observed by another wafer or mask inspecting apparatus, moving the field of view of the electron microscope to the area where said fault or object exists, and displaying the coordinates of faults or objects which were obtained by another wafer or mask inspecting apparatus, the field-of-view of the electron microscope and its vicinity, a function of a pointing device switch which moves the field-of-view of the electron microscope to a position which is pointed to by a pointer on said display, and a function of changing the display as said field-of-view moves.

7 Claims, 10 Drawing Sheets

ELECTRON MICROSCOPE

CROSS REFERENCE TO RELATED APPLICATIONS

This is a continuation of application Ser. No. 09/811,719 filed Mar. 19, 2001 now abanoded, which is incorporated herein by reference in its entirety.

BACKGROUND OF THE INVENTION

The present invention relates to an electron microscope for observing or detecting a surface or inside of a semiconductor wafer or a mask for exposing a semiconductor pattern for faults and/or foreign objects, particularly to an electron microscope for observing or detecting a surface or inside using coordinates of faults and/or faults which were measured by another wafer/mask inspecting apparatus.

Faults or objects on a semiconductor wafer or a mask for exposing a semiconductor pattern may give fatal problems to the semiconductor performances and reduce the efficiency of production of semiconductors.

Therefore, to increase the production efficiency of semiconductors, it is required to remove unwanted objects from wafers and masks and faults from semiconductor patterns or mask patterns on the wafers as much as possible. Therefore, it is thought to be very important to detect and observe wafers and masks for faults and/or objects (hereinafter generically described as faults) in the production of semiconductors and analyze the causes of the faults.

Recently, semiconductors have become smaller and smaller and their performance may be seriously damaged by even a fault of about 0.1 micron on a wafer. Conventionally an optical fault inspector or an optical object inspector (hereinafter generically described as an inspector) is used to locate faults on a wafer, move the field of view of the electron microscope to the location where the faults exist according to information on fault coordinates or the like obtained by said inspector, observe and identify the fault.

However, a wafer/mask area to be observed at a time at a magnification is limited although it is dependent upon the size of a display screen of the electron microscope. Therefore, if fault coordinates measured by another inspector contain errors, the fault cannot be caught in the field of view of the electron microscope.

Although various techniques have been supported to eliminate coordinate errors between the electron microscope and another inspector, such techniques cannot assure coordinate accuracies high enough to capture all faults in the field of view of the electron microscope.

To search faults, the operator gradually moves the field of view of the electron microscope using a pointing device (such as a mouse or a trackball) according to fault coordinates measured by another inspector and the location of the field of view of the electron microscope in reference to a wafer map, a die/chip diagram or an optical microscope image which is displayed separately. The conditions of observation of the electron microscope (such as a magnification) is calculated and set from data obtained by another inspector.

However, at a high magnification, for example, ×10,000 of the electron microscope, said conventional techniques do not have any means to show where the observation is made now and it is very difficult to move the field of view of the electron microscope to a position for observation.

Further, to detect target faults in the field of view of the electron microscope or to set conditions of observation for the field, the conventional technique must calculate observation conditions such as a magnification for each fault from numeric data obtained by another inspector.

Further, the conventional technique cannot use coordinate errors obtained in search of a fault easily for search of other faults, searching of the conventional technique is not efficient.

Furthermore, in case both an area which was already observed by an electron microscope and an area which has not been observed are separately displayed on-screen, it sometimes happened that the conventional technique could not change conditions of observation of the electron microscope or involuntarily initialized displays.

SUMMARY OF THE INVENTION

An object of the present invention is to solve the aforesaid problems and to provide an electron microscope which enables the operator to move and set the field of view onto an area having a fault easily and accurately.

To attain the aforesaid object, the present invention is characterized by the following.

In accordance with the present invention, an electron microscope for observing a surface or inside of a semiconductor wafer or a mask for exposing a semiconductor pattern for faults and/or foreign objects comprises a function of loading measurement data of coordinates or sizes of faults or objects which were observed by another wafer or mask inspecting apparatus, moving the field of view of the electron microscope to the area where said fault or object exists, and displaying the coordinates of faults or objects which were obtained by another wafer or mask inspecting apparatus, the field of view of the electron microscope and its vicinity, a function of a pointing device switch which moves the field of view of the electron microscope to a position which is pointed to by a pointer on said display, and a function of changing the display as said field of view moves.

The electron microscope in accordance with the present invention can display fault coordinates obtained by another inspector, the field of view of the electron microscope and its vicinity, enlarge or shrink the views by operation of a pointing device or according to the movement of the field of view of the electron microscope or move the vicinity at a constant magnification.

Further, the operator can move the field of view of the electron microscope by pointing to a desired position on the view with a pointing device.

This enables the operator to know the position or area which is now observed and to move the field of view of the electron microscope easily to an area near the fault coordinates obtained by another inspector.

Further, fault sizes are displayed on a screen showing the field of view and the display is changed according to the condition of observation of the electron microscope.

Therefore, the operator can set conditions of fault observation for the field of view of the electron microscope and detect faults in the field of view according to the fault shapes.

Furthermore, the electron microscope in accordance with the present invention has a function of displaying fault coordinates and distances of the field of view obtained by another inspector, storing the values, and moving the field of view of the electron microscope relatively by the stored distances.

This function enables a coordinate error in a fault searching to be used for search of another fault and increase the efficiency of searching.

Both an area which was already observed by an electron microscope and an area which has not been observed are separately displayed on-screen. These views are changed when the conditions of observation of the electron microscope are changed.

This enables efficient observation of non-observed areas only independently of conditions of observation of the electron microscope and prevents incomplete observation.

DETAILED DESCRIPTION OF THE INVENTION

One embodiment of the present invention will be explained below with reference to the accompanying drawings. This embodiment uses a three-button mouse as a pointing device. However, it is not intended as a definition of the limits of the present invention.

Figure 1:
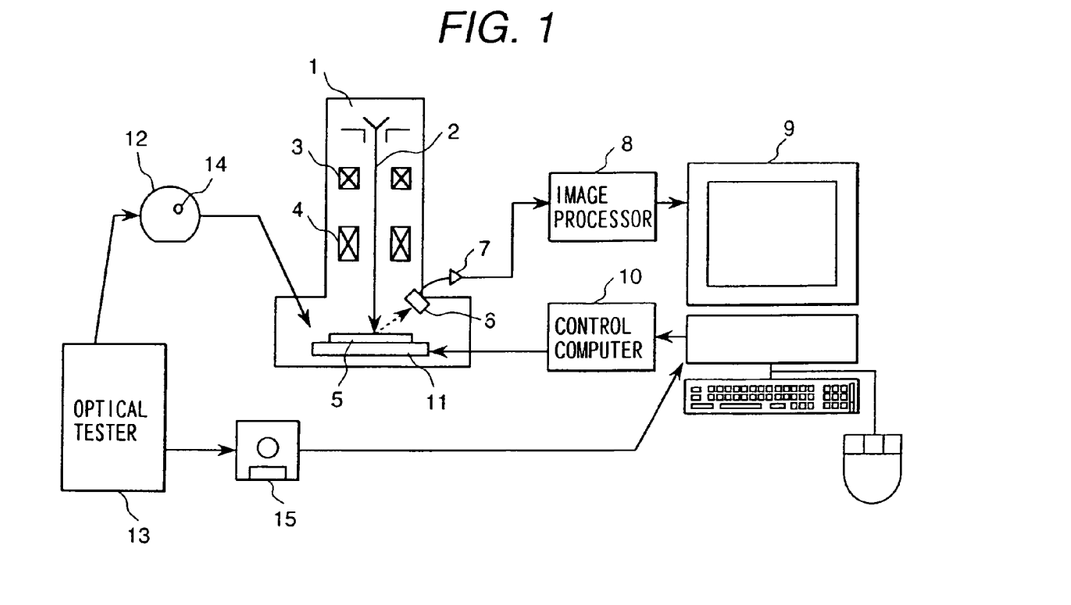
FIG. 1 is a schematic view of a system configuration of a scanning electron microscope which is an embodiment of the present invention.

FIG. 1 is a schematic view of a system configuration of a scanning electron microscope 1, which is an embodiment of the present invention. Electron beams emitted from an electron gun 2 are condensed by an electron lens 3, scanned and deflected 2-dimensionally by a defector 4, and applied to a specimen 5. When hit by the electron beams, the specimen generates secondary particles such as reflected electrons and secondary electrons according to the shape and material of the specimen. These secondary electrons are detected by a detector 6 and amplified by an amplifier 7.

A signal output from the amplifier 7 is AID-converted into a digital image data by an image processor 8 and the digital image data is displayed in real time on the CRT of a workstation or a personal computer 9.

The workstation or the personal computer 9 is connected to a computer for controlling the electron microscope by a transmission medium (not visible in FIG. 1). The operator can submit various commands from the workstation or the personal computer 9 to the controlling computer 10 to move the specimen stage 11 of the electron microscope. As the specimen stage 11 moves, the field of view of a specimen 5 also moves on the CRT of the workstation or the personal computer 9.

A semiconductor wafer or mask 12 is sent to an optical inspecting apparatus 13 (another wafer/mask inspector) and undergoes a fault inspection to detect faults 14 on the wafer or mask 12. The optical inspecting apparatus 13 collects information about coordinates and sizes of faults 14 on the wafer or mask and outputs the result.

The wafer or mask 12 inspected by the optical inspecting apparatus 13 is set on the specimen stage 11 of said electron microscope. At the same time, the result of inspection made by the optical inspecting apparatus 13 is sent in an information medium (transmission, floppy disk, MO, etc.) to the workstation or the personal computer 9 of the electron microscope.

The workstation or the personal computer 9 corrects the coordinates of the wafer or mask on the specimen stage of the electron microscope according to the coordinate information in said inspection result. Next, the specimen stage 11 of the electron microscope, that is the field of view, is moved to the coordinates on which a fault 14 exists and the obtained microscope image is displayed on the CRT of the workstation or the personal computer 9.

Figure 2:
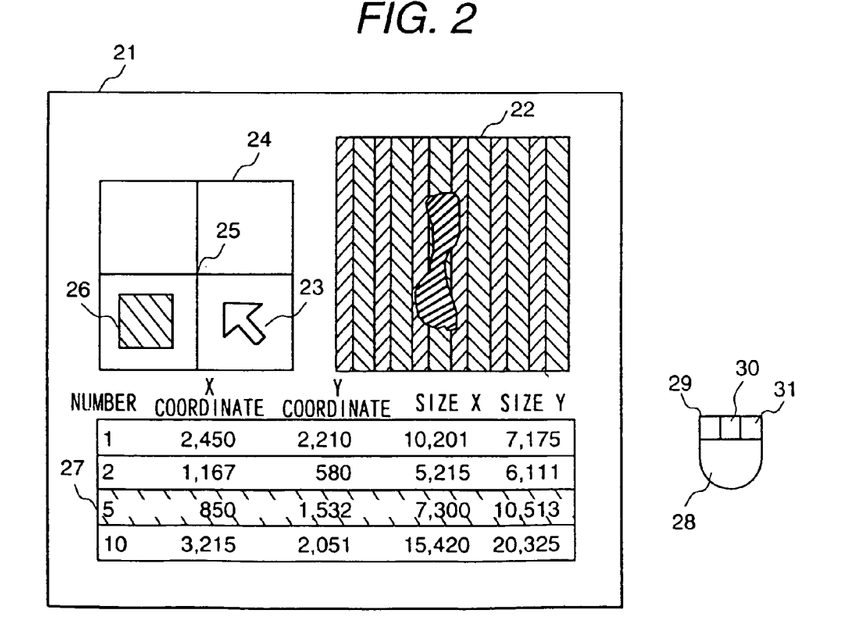
FIG. 2 shows a schematic screen layout of the CRT of the workstation or a personal computer to operate the electron microscope of the present invention, including a field-of-view and a vicinity field.

FIG. 2 shows a schematic screen layout of the CRT of the workstation or a personal computer 9. This screen shows detailed information, the field of view, and its vicinity.

The CRT screen 21 which is the display screen of the present invention shows an electron microscope image and the graphical user interface (GUI) for the operator. The CRT screen comprises a field for an electron microscope image 22, a field for a pointer 23 as a pointing device, a field for a field-of-view 26 of the electron microscope, a field for a vicinity 24 of the field of view of the electron microscope, a field for the center coordinates 25, and a field for a list 27 of inspection results of faults obtained by the optical inspecting apparatus 13. The field-of-view 26 of the electron microscope shows an observation area including the electron microscope image 22.

Data obtained by the optical inspecting apparatus 13 contains the coordinates and size of each fault detected by the optical inspecting apparatus. The field for a vicinity 24 of the field of view of the electron microscope shows fault positions and sizes according to these kinds of information. These kinds of information obtained by the optical inspecting apparatus 13 are stored in the storage means of the workstation or the personal computer 9.

The pointing device to operate the GUI on the CRT screen 21 is a three-button mouse 28 having a left button 29, a center button 30, and a right button 31.

The operator follows a procedure explained below to search for a fault. The operator first selects a fault in the fault list 27, clicks the left button 29 of the mouse on it. The field of view of the electron microscope moves to the coordinates of the selected fault.

The view of the area to which the field of view positions is displayed in the electron microscope image field 22. At the same time, the coordinates of the fault selected from the list is placed in the center 25 of the vicinity field 24 and the field of view 26 is displayed in the vicinity field to indicate the position of the field of view relative to the center coordinates.

In some cases, a selected fault is not found in the new field of view at the coordinates of the fault selected from the list, which is obtained by the optical inspecting apparatus. This is because of unreliable fault coordinates obtained by the optical inspecting apparatus, errors of the specimen stage of the electron microscope, or a difference between the magnification of the optical microscope and the magnification of the electron microscope. In this case, the operator moves the field of view 26 of the electron microscope to the vicinity of the fault, that is, towards the center of coordinates 25, which indicate the coordinates of the fault obtained by the optical inspecting apparatus.

With this, the operator can recognize the position or area of the current field of view of the electron microscope relative to the fault coordinates obtained by the optical inspecting apparatus at a glance and easily move the field of view of the electron microscope at a high magnification around the fault coordinates obtained by the optical inspecting apparatus where a fault must exist.

[Embodiment 1]

Below will be explained an embodiment of the present invention which enlarges or shrinks the field of view of the electron microscope and its vicinity.

Figure 3:
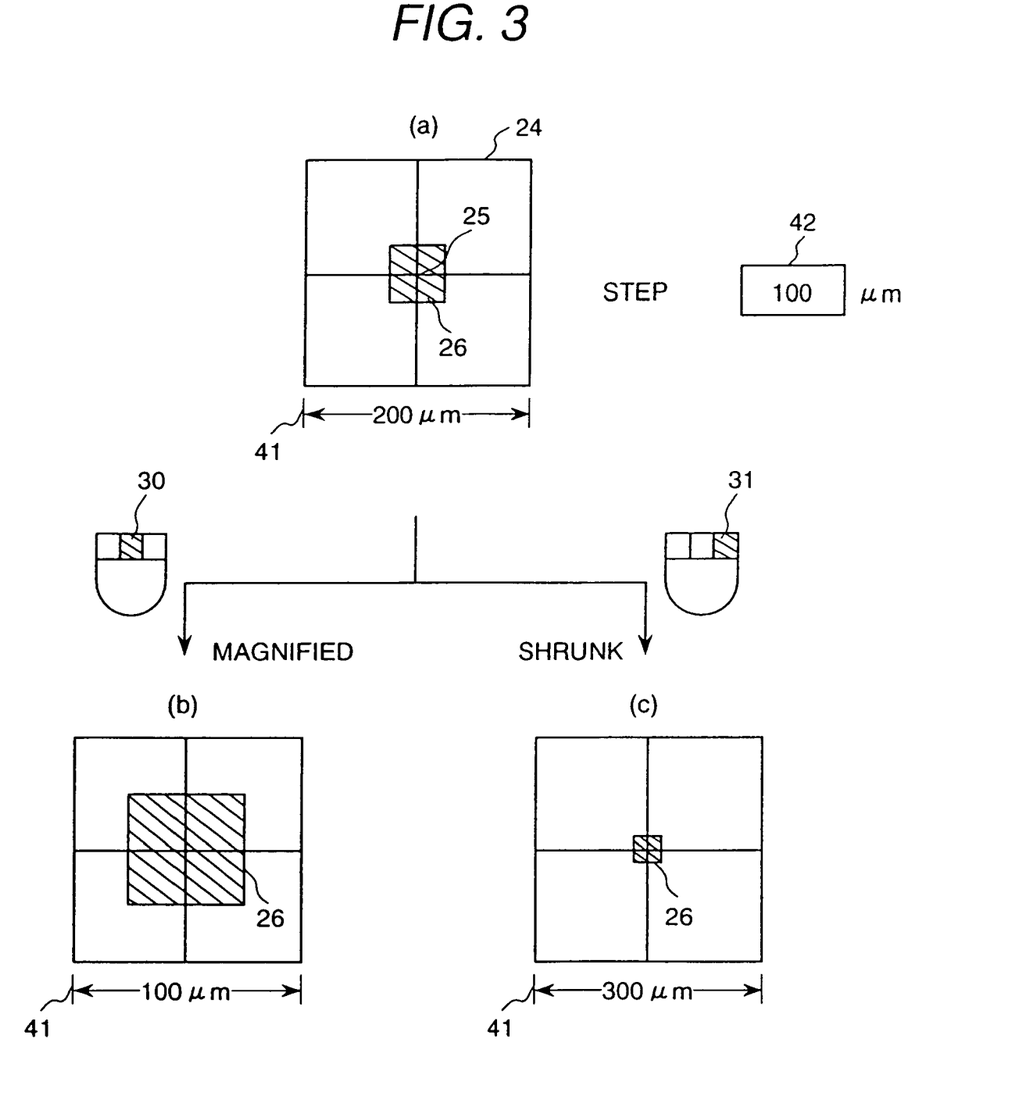
FIG. 3 is an illustration explaining a procedure of enlarging or shrinking the field-of-view and its vicinity of the electron microscope of Embodiment 1.
Figure 4:
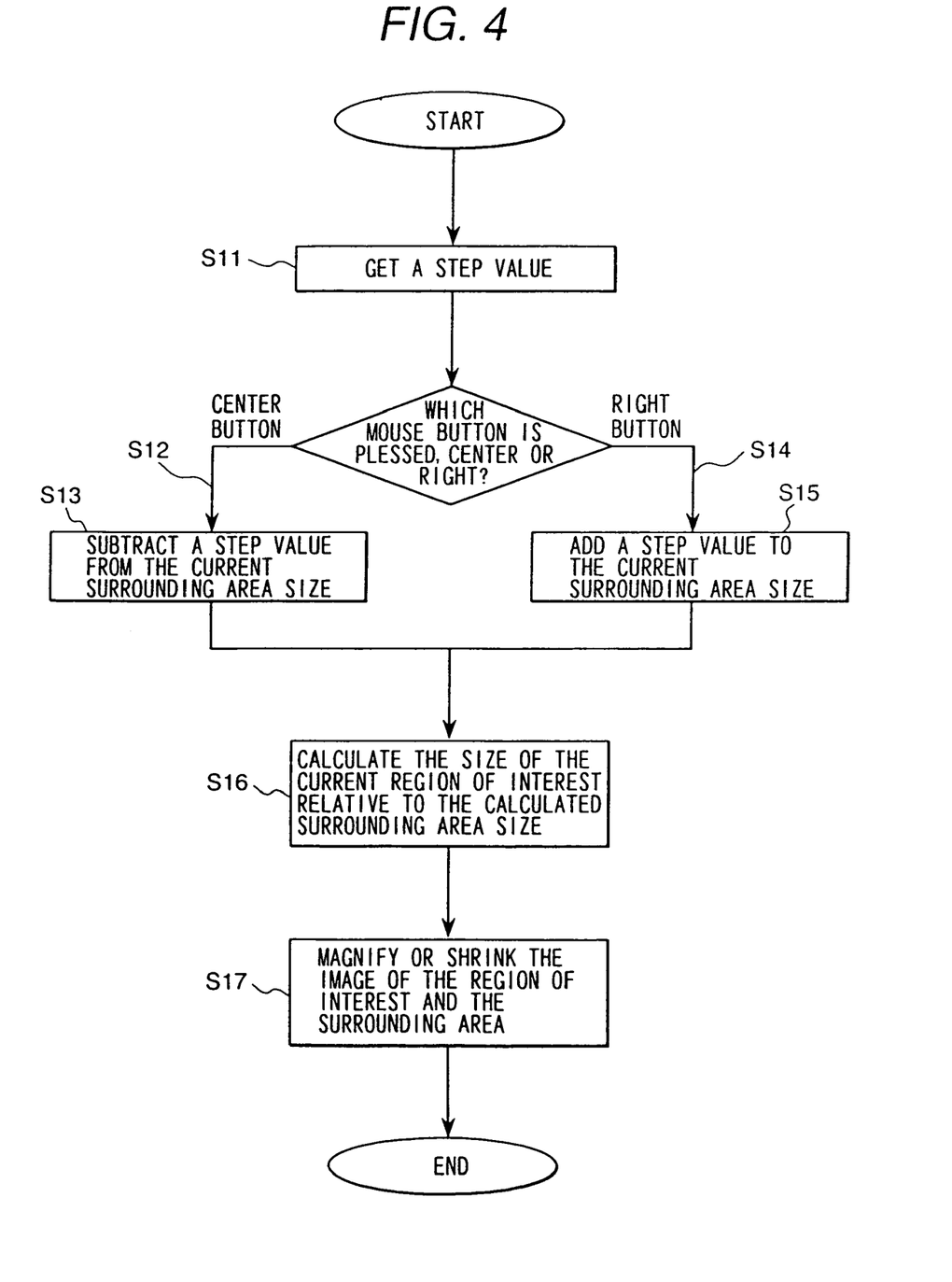
FIG. 4 is a flowchart explaining a procedure of enlarging or shrinking the field-of-view and its vicinity of the electron microscope of Embodiment 1.

FIG. 3 is an illustration for explaining a procedure of enlarging or shrinking the field of view of the electron microscope and its vicinity and FIG. 4 shows its flowchart.

The operator moves the field of view of the electron microscope to the fault coordinates obtained by the optical inspecting apparatus. The field for the field-of-view 26 of the electron microscope, the vicinity field 24, the center of coordinates 25, and the actual size 41 of the vicinity field are displayed on-screen.

By clicking the center button 30 or the right button 31 of the mouse anywhere in the vicinity field 24, the operator gets a step value 42 to change the actual size 41 of the vicinity field (S11). The operator can enter any step value.

When the operator clicks the center button 30 (S12), the workstation or personal computer subtracts a step value from the current actual size 41 of the vicinity field and gets a new vicinity field size (S13).

Next, the workstation or personal computer calculates the display size of the field of view 26 of the electron microscope relative to the new vicinity field (S16) and displays the enlarged field-of-view and the enlarged vicinity field as shown in FIG. 3(b) (S17).

When the operator clicks the right button 31 (S14), the workstation or personal computer adds a step value to the current actual size 41 of the vicinity field and gets a new vicinity field size (S15).

Next, the workstation or personal computer calculates the display size of the field-of-view 26 of the electron microscope relative to the new vicinity field (S16) and displays the shrunk field-of-view and the shrunk vicinity field as shown in FIG. 3(c) (S17).

This function enables the operator to specify the rate of enlargement or shrinkage of the vicinity field of the fault coordinates obtained by another inspecting apparatus by numeric values. Accordingly, in case the deviation of fault coordinates can be estimated according to the types of optical inspecting apparatus or in case the deviation of fault coordinates can be estimated for each unit on a wafer, the operator can change sizes of the vicinity field and search a target fault efficiently.

Further, the operator can recognize the size of the field-of-view relative to the vicinity field at a glance and estimate the number of fields-of-view required to observe before searching the result. This can easily tell the quantity of works required for searching.

[Embodiment 2]

Figure 5:
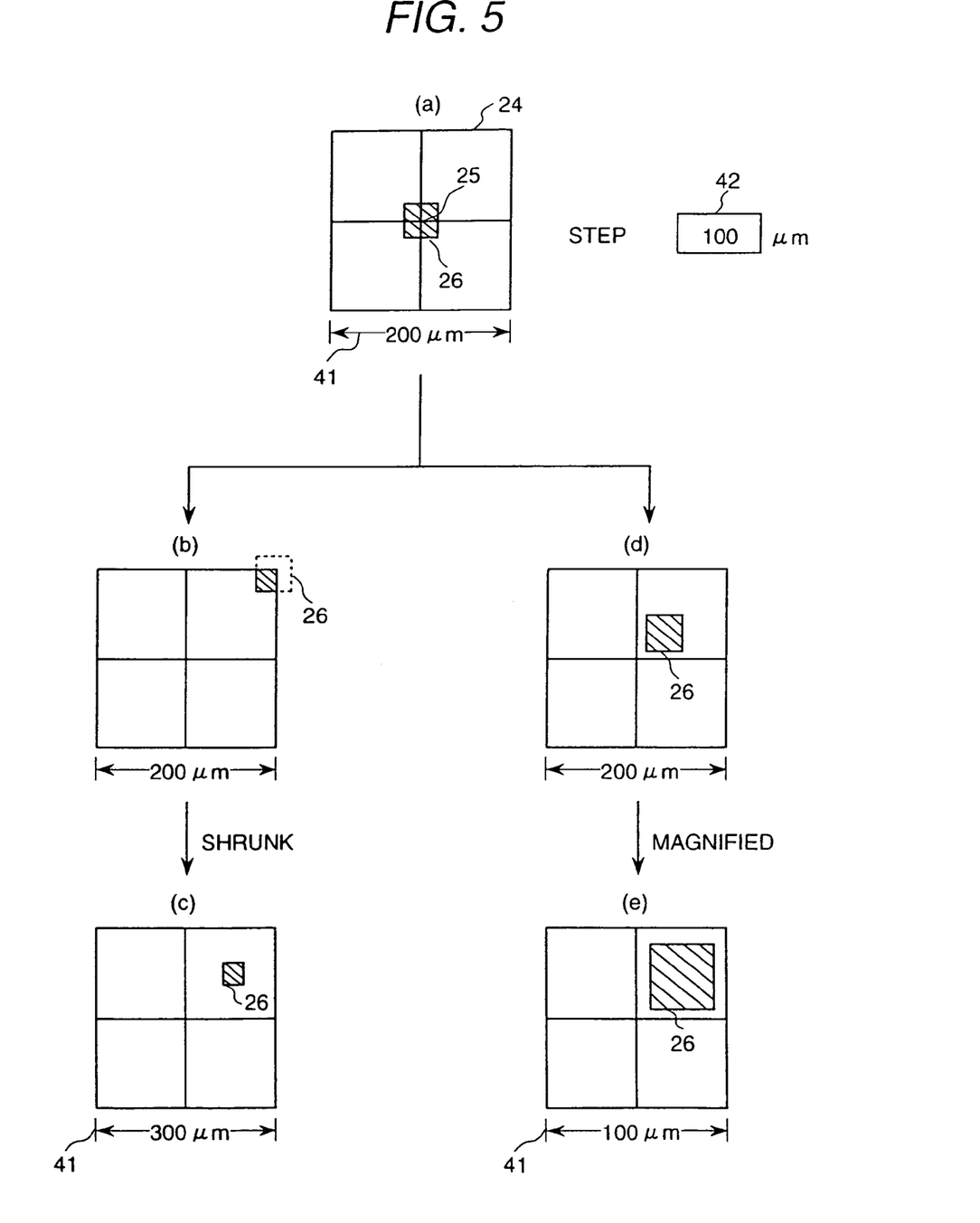
FIG. 5 is an illustration explaining a procedure of enlarging or shrinking the field-of-view and its vicinity of the electron microscope of Embodiment 2.
Figure 6:
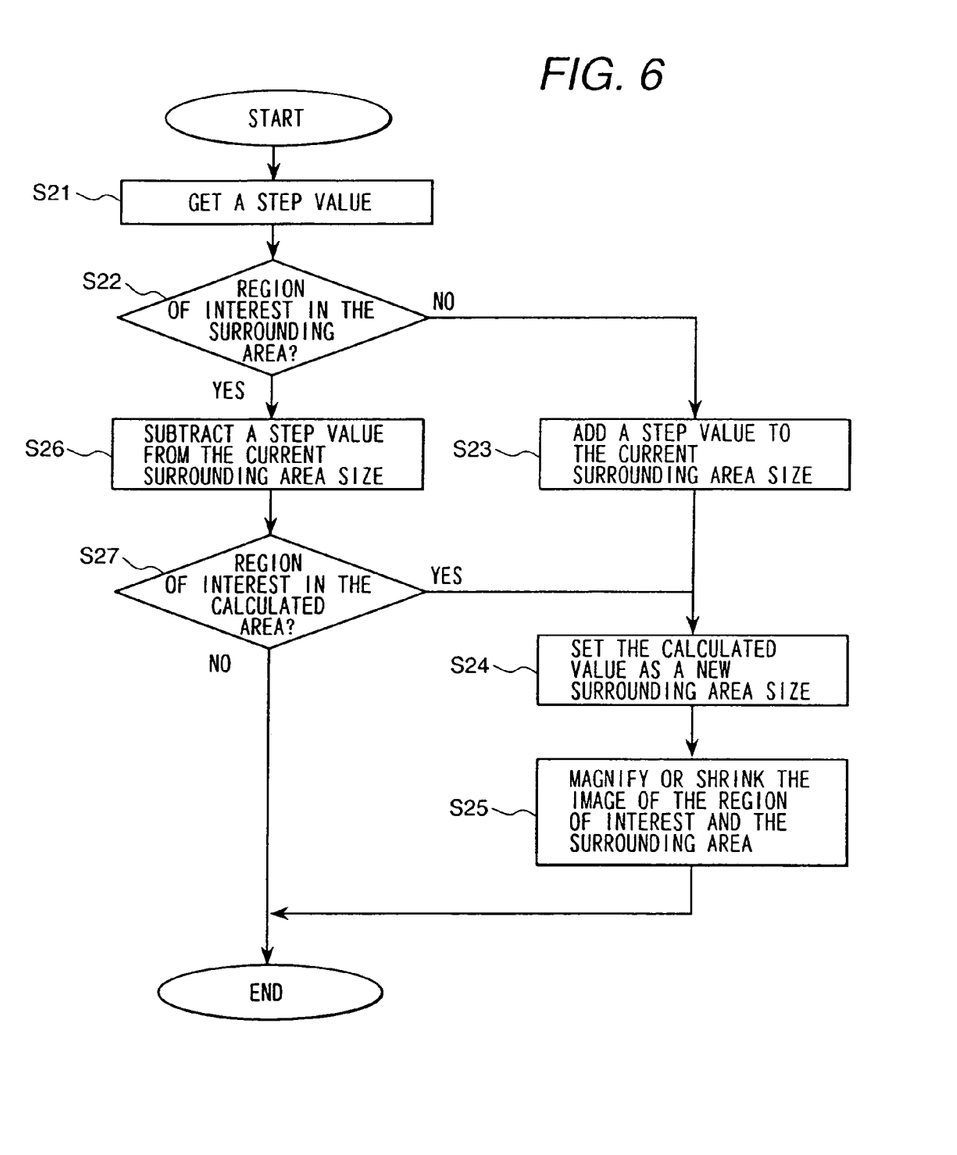
FIG. 6 is a flowchart explaining a procedure of enlarging or shrinking the field-of-view and its vicinity of the electron microscope of Embodiment 2.

Below will be explained a second embodiment of the present invention which enlarges or shrinks the field-of-view of the electron microscope and its vicinity. FIG. 5 is an illustration for explaining a procedure of enlarging or shrinking the field-of-view of the electron microscope and its vicinity and FIG. 6 shows its flowchart.

The operator moves the field-of-view of the electron microscope to the fault coordinates obtained by the optical inspecting apparatus. Referring to FIG. 5(a), the field-of-view 26 of the electron microscope, the vicinity field 24, the center of coordinates 25, and the actual size 41 of the vicinity field are displayed on-screen.

In some cases, a selected fault is not found in the new field-of-view at the coordinates of the fault selected from the list, which is obtained by the optical inspecting apparatus 13. This is because of unreliable fault coordinates obtained by the optical inspecting apparatus, errors of the specimen stage of the electron microscope, or a difference between the magnification of the optical microscope and the magnification of the electron microscope.

In such a case, to observe a target fault as an electron microscope image, the electron microscope of this embodiment enlarges or shrinks the vicinity field 24 as the field-of-view 26 moves without changing the field-of-view 26 in the vicinity field 24.

The operator moves the field-of-view by operating the pointing device and gets a step value to enlarge or shrink the vicinity field (S21). The operator can enter any step value.

Next, the workstation or personal computer checks whether the new field-of-view (after movement) is in the vicinity field. As shown in FIG. 5(b), if the field of view 26 is not in the vicinity field, the entered step value 42 is added to the actual size of the current vicinity field size (S23). As shown in FIG. 5(c), the result is used as the actual size 41 of a new vicinity field (S24). With this, the new shrunk field-of-view and the new shrunk vicinity field are displayed (S25).

When the field-of-view is in the vicinity field, the entered step value 42 is subtracted from the actual size 41 of the current vicinity field (S26).

Next, the workstation or personal computer checks whether the new field-of-view (after movement) is in the vicinity field (S27). If the field-of-view 26 is in the vicinity field as shown in FIG. 5(d), the new enlarged field-of-view and the new enlarged vicinity field are displayed (S25) with the result of calculation as the actual size 41 of a new vicinity field (S24) as shown in FIG. 5(e).

In the other cases, the actual size 41 of the vicinity field is not changed and the field-of-view and the vicinity field will be neither enlarged nor shrunk.

Each time the operator moves the field-of-view to detect a fault in the field-of-view, the above steps are repeated.

With this, the field around the fault coordinates is enlarged or shrunk with the field-of-view displayed on-screen even when the field of view of the electron microscope is moved to anywhere. Therefore, even when a deviation from the fault coordinate cannot be estimated in advance, the operator can recognize the positional relationship between the fieldof-view of the electron microscope and the fault coordinates obtained by another inspecting apparatus just by moving the field of view and can search for faults easily.

[Embodiment 3]

Figure 7:
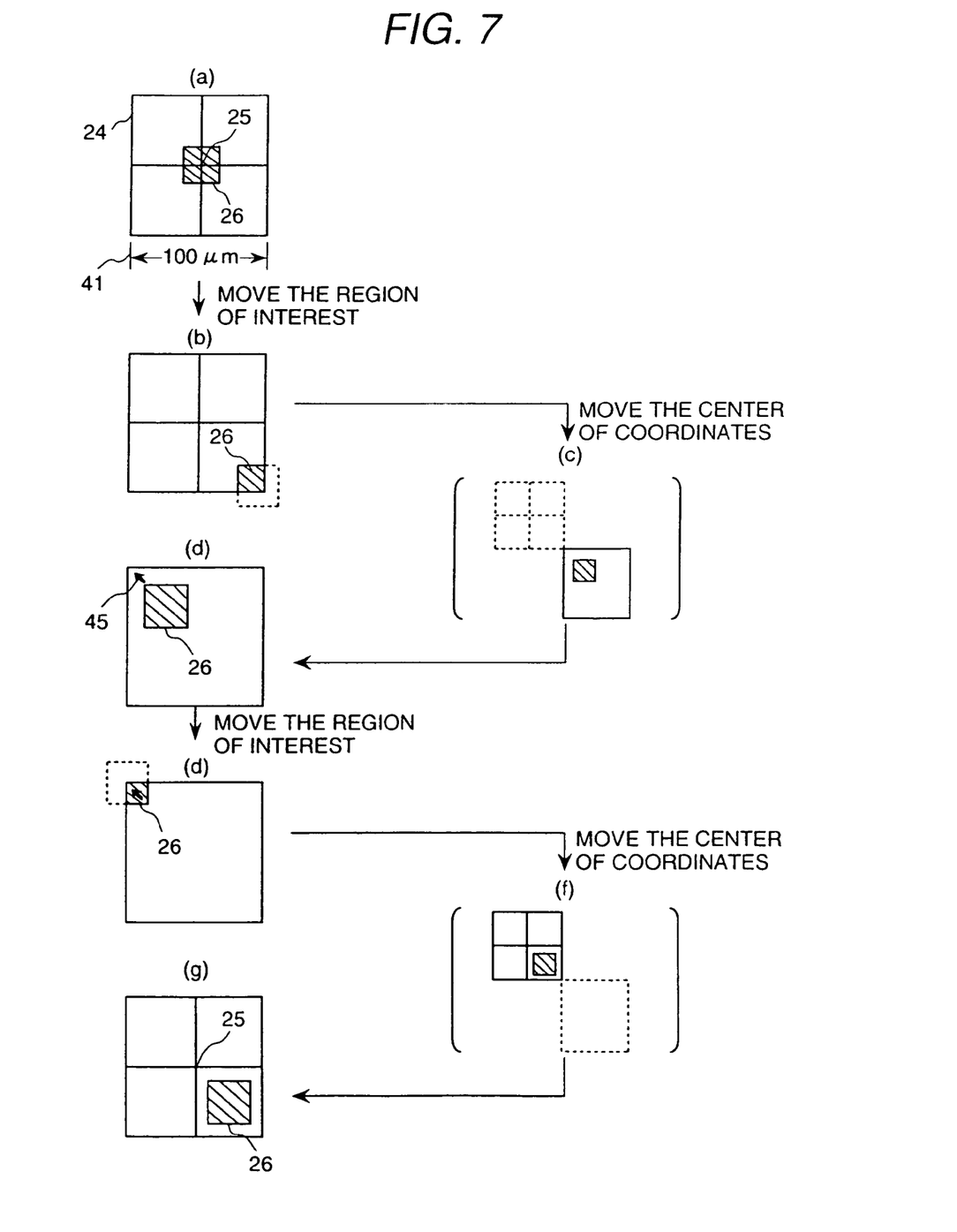
FIG. 7 is an illustration explaining a procedure of moving the vicinity field according to the movement of the field-of-view in Embodiment 3.
Figure 8:
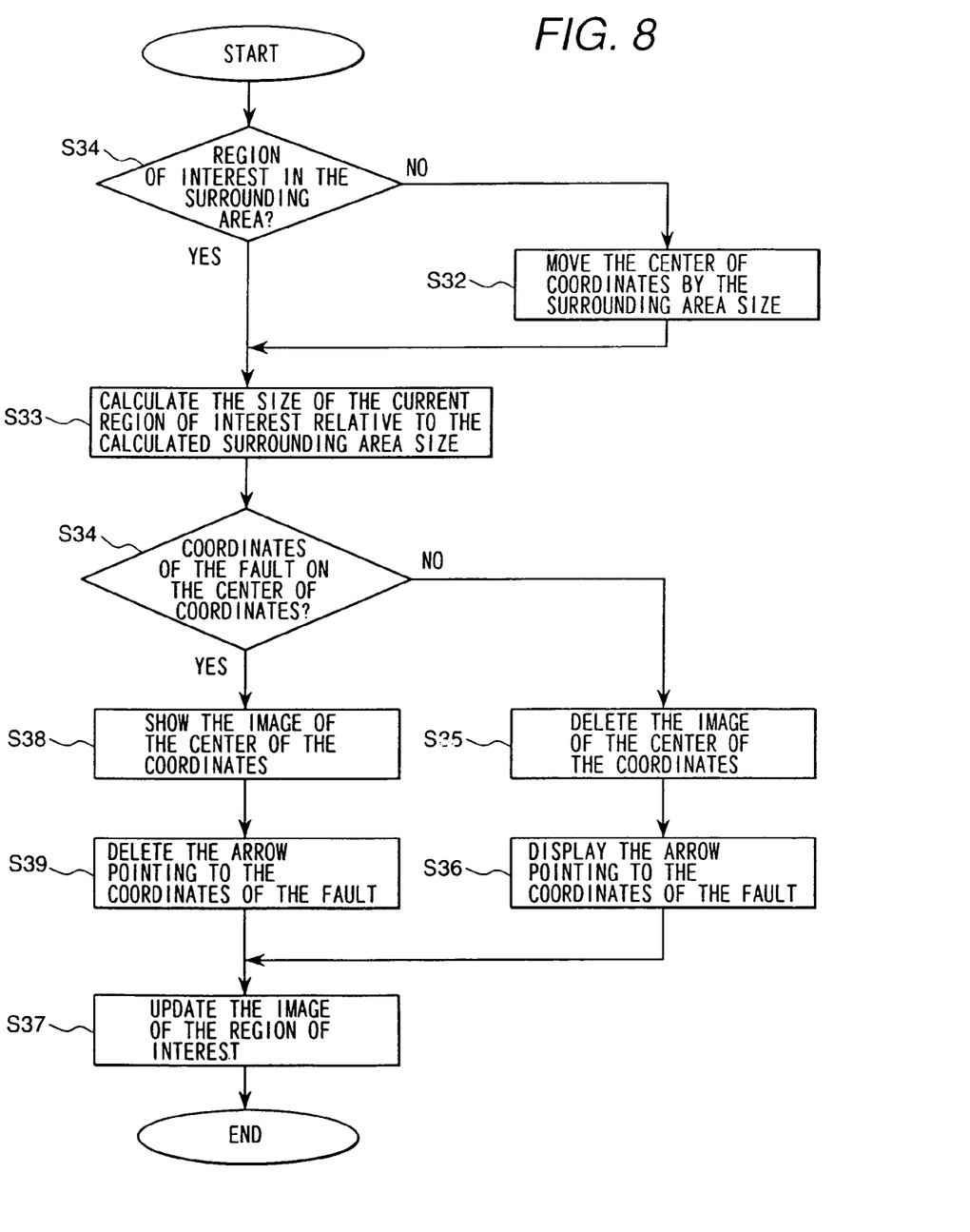
FIG. 8 is a flowchart explaining a procedure of moving the vicinity field according to the movement of the field-of-view in Embodiment 3.

Below will be explained a third embodiment of the present invention which moves the vicinity field without changing the magnitude of the field-of-view of the electron microscope and the magnitude of the vicinity field. FIG. 7 is an illustration for explaining a procedure of moving the vicinity field according to the movement of the field-of-view and FIG. 8 shows its flowchart.

The operator moves the field-of-view of the electron microscope to the fault coordinates obtained by the optical inspecting apparatus. Referring to FIG. 7(*a*), the field for the field-of-view 26 of the electron microscope, the vicinity field 24, the center of coordinates 25, and the actual size 41 of the vicinity field are displayed on-screen.

Similarly to the above embodiments, a selected fault is not found in the new field-of-view at the coordinates of the fault obtained by the optical inspecting apparatus and the deviation cannot be estimated.

To get an electron microscope image of a target fault in such a case, this embodiment moves the center coordinates 25 in the vicinity field 24 as the field-of-view 26 of the electron microscope moves while keeping the field-of-view displayed in the vicinity field 24.

After the operator moves the field-of-view by operating the pointing device, the workstation or personal computer checks whether the new field-of-view (after the movement) is in the vicinity field (S31). If the field-of-view 26 is not in the vicinity field as shown in FIG. 7(*b*), the current center coordinates is moved by the actual size 41 of the vicinity field along the movement of the field-of-view as shown in FIG. 7(*c*) (S32).

Next, the workstation or personal computer calculates the position of the field-of-view relative to the center coordinates 25 (S33) and checks whether the center coordinates 25 are equal to the fault coordinates obtained by another inspecting apparatus (S34). If the center coordinates are not equal to the fault coordinates, the workstation or personal computer deletes the center coordinates 25 as shown in FIG. 7(*d*) (S36), displays an arrow 45 oriented to the fault coordinates obtained by the optical inspecting apparatus (S36), and updates the display of the field-of-view 26 (S37).

If the field-of-view moves out of the vicinity field as shown in FIG. 7(*e*), the center coordinates 25 is moved by the actual size 41 of the vicinity field as shown in FIG. 7(*f*) (S32).

When the new center coordinates 25 (after this movement) match with the fault coordinates obtained by another optical inspecting apparatus, the workstation or personal computer displays the center coordinates 25 as shown in FIG. 7(*g*) (S38), deletes the arrow 45 which is oriented to the fault coordinates obtained by the optical inspecting apparatus (S39), and updates the display of the field-of-view 26 (S37).

Each time the operator moves the field of view to detect a fault in the field-of-view, the above steps are repeated.

With this, the center coordinates are moved by the actual size of the vicinity field without changing the display size of the field-of-view of the electron microscope while the field-of-view is moved anywhere. Further this embodiment indicates a direction in which the fault coordinates obtained by the optical microscope exist. This enables the operator to search faults in each field of an accessible size without fail.

[Embodiment 4]

Figure 9:
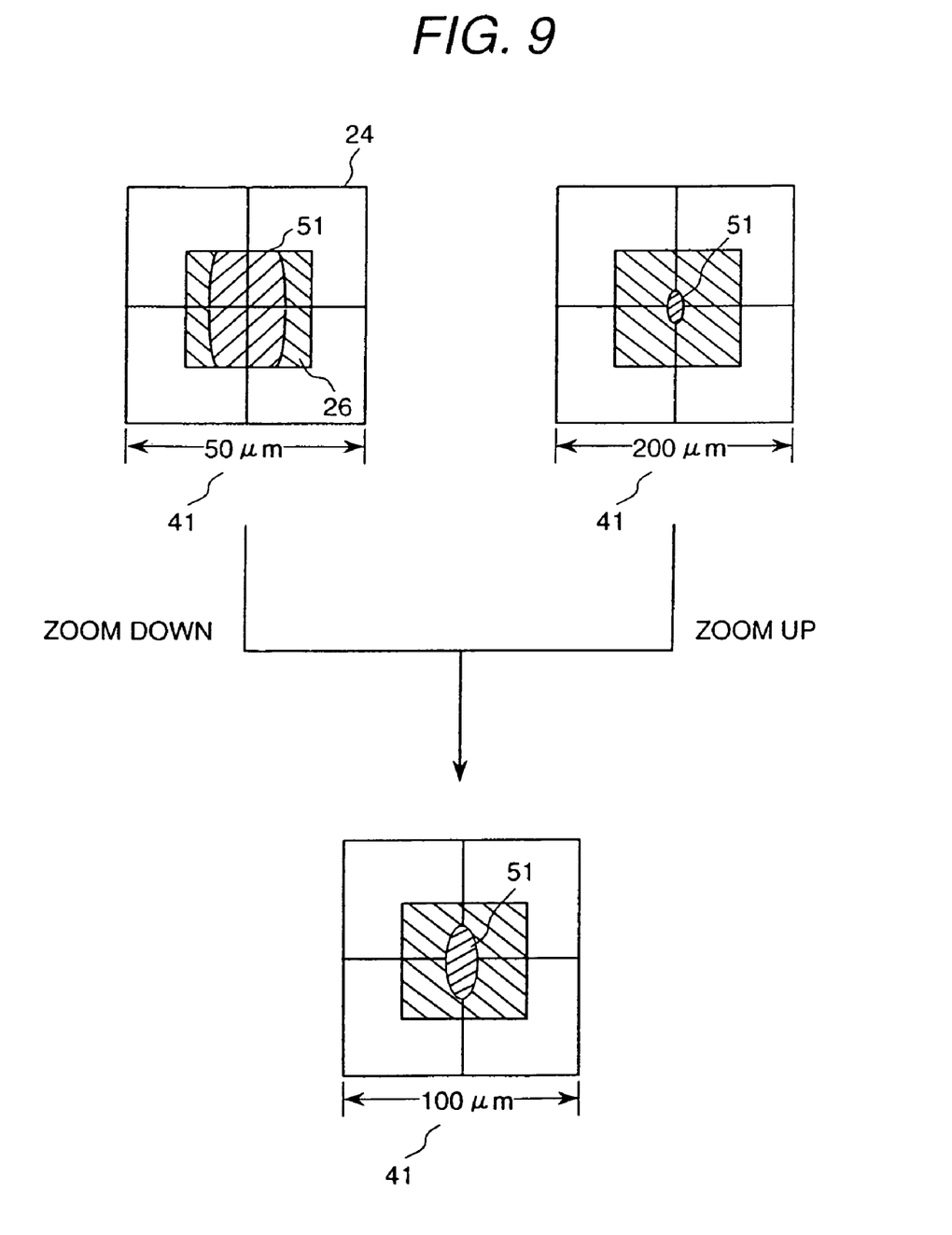
FIG. 9 is a schematic diagram explaining a procedure of displaying a fault in the field-of-view of Embodiment 4.

FIG. 9 shows an example of displaying a fault in the field-of-view in accordance with the present invention.

The workstation or the personal computer calculates the size of a fault in the field-of-view 26 within the vicinity field 24 from X and Y coordinates of a fault obtained by an optical inspecting apparatus and displays the shape 51 (e.g. an ellipse) of the fault in the field-of-view 26. The fault can have any shape (e.g. a rectangle).

If information about fault shapes and compositions are available from the optical inspecting apparatus 13, it is also possible to simulate so that the composition information can be recognized.

When the magnification of the electron microscope image is reduced, the actual size 41 of the vicinity field is increased in inverse proportion to the magnification and the shape 51 of the fault is reduced with the display ratio of the field-of-view 26 to the vicinity field 24 unchanged.

When the magnification of the electron microscope image is increased, the actual size 41 of the vicinity field is decreased in inverse proportion to the magnification and the shape 51 of the fault is increased with the display ratio of the field-of-view 26 to the vicinity field 24 unchanged.

With this, the operator can get the relative size of a fault in the field-of-view at a selected magnification of the electron microscope. Therefore, even when a fault is not actually in the field of view, the operator can set a magnification of the electron microscope fit for searching or observation.

As the shape of a fault is displayed in the field-of-view of the electron microscope, the operator can easily recognize a target fault when the fault is hard to be distinguished from a pattern or a plurality of faults exist in the field-of-view.

[Embodiment 5]

Figure 10:
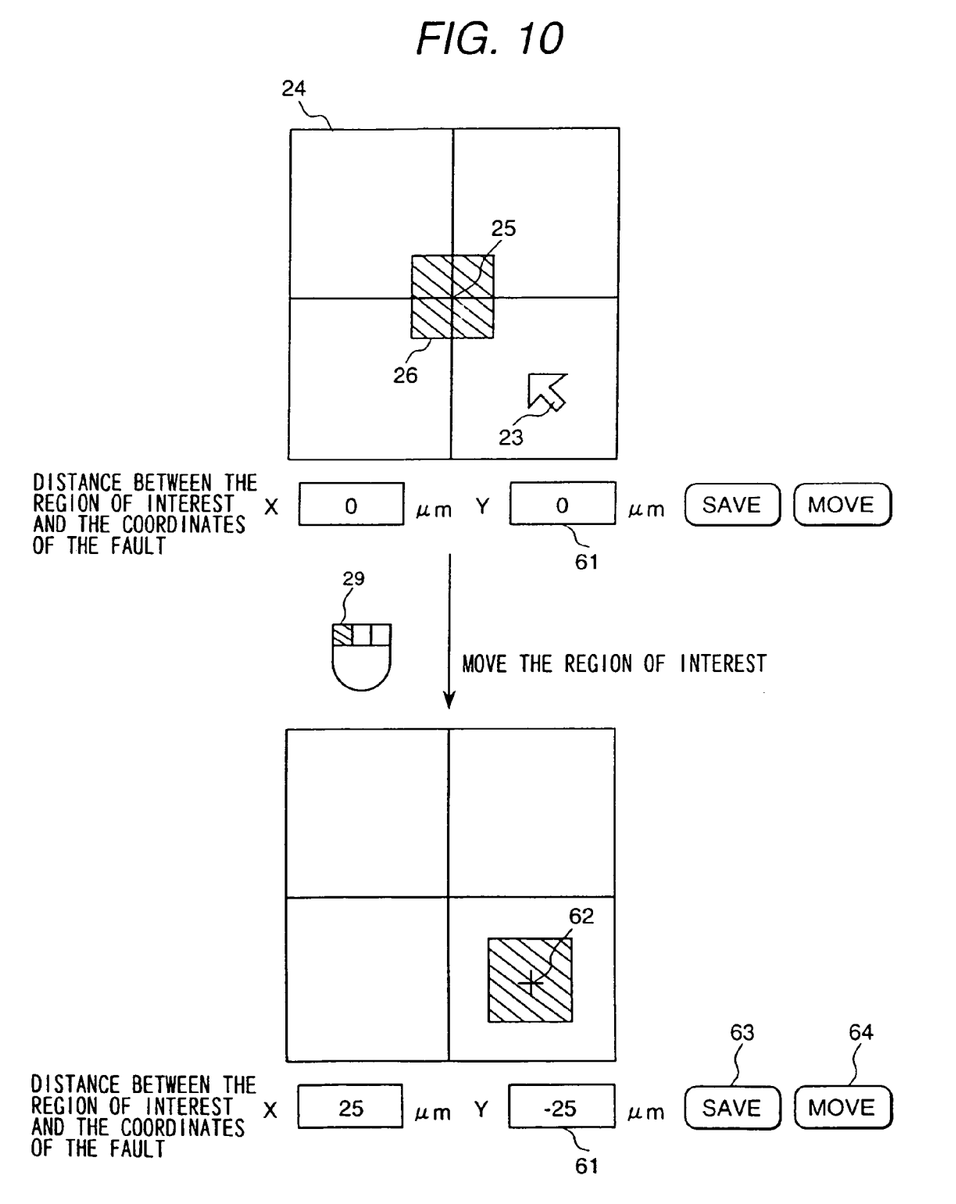
FIG. 10 is a schematic diagram explaining a movement of the field-of-view of the electron microscope of Embodiment 5 and a procedure of displaying a distance between the fault coordinates and the center of the field-of-view.

FIG. 10 shows an example of moving the field-of-view of the electron microscope and displaying a distance between the center of the field-of-view and the fault coordinates.

The operator moves the field-of-view of the electron microscope toward the fault coordinates obtained by the optical inspecting apparatus 13.

The field-of-view 26 of the electron microscope, the vicinity field 24, the center of coordinates 25, and the distance 61 between the center of the field-of-view and the fault coordinates are displayed on-screen.

In this status, the center coordinates 25 of the field-of-view matches with the center coordinates 25 of the vicinity field 24. Therefore, the distance between the center of the field-of-view and the fault coordinates is X=0 and Y=0.

When the operator moves the pointer 23 (of the pointing device) to a position in the vicinity field 24 to which the operator wants to move the field-of-view of the electron microscope and clicks the left button 29 of the mouse, the field-of-view of the electron microscope moves to the selected position. The workstation or the personal computer calculates the distance between the center coordinates 25 of the vicinity field 24 and the center coordinates 62 of the field-of-view and displays the result in the "Distance between the region of interest and the coordinates of the fault" field 61.

When the operator clicks the SAVE button 63, the values set in the "Distance between the region of interest and the coordinates of the fault" field 61 are saved. Next, the operator moves the field of view to another set of fault coordinates and clicks the MOVE button 64. The field-of-view of the electron microscope is relatively moved by a distance which was saved latest.

As explained above, the operator can easily move the field-of-view of the electron microscope to any place near the fault coordinates. Therefore, this embodiment is very effective to move the field-of-view of the electron microscope directly and easily to any place near the fault coordinates in case a deviation of a fault is estimated.

With this, when a fault is detected in the field-of-view, the operator can get the distance between the fault coordinates obtained by the optical inspecting apparatus 13 and the actually-observed fault coordinates easily from the content in the "Distance between the region of interest and the coordinates of the fault" field 61. This is very effective when the fault coordinates obtained by the optical inspecting apparatus 13 are not reliable or affected by a stage error. This embodiment can correct such overall coordinate errors between the optical inspecting apparatus 13 and the electron microscope in accordance with the present invention.

Further, if it is assumed that the other fault has almost the same error, the operator can search the fault efficiently by moving the field-of-view of the electron microscope to the same deviated position by simple button operations.

[Embodiment 6]

Figure 11:
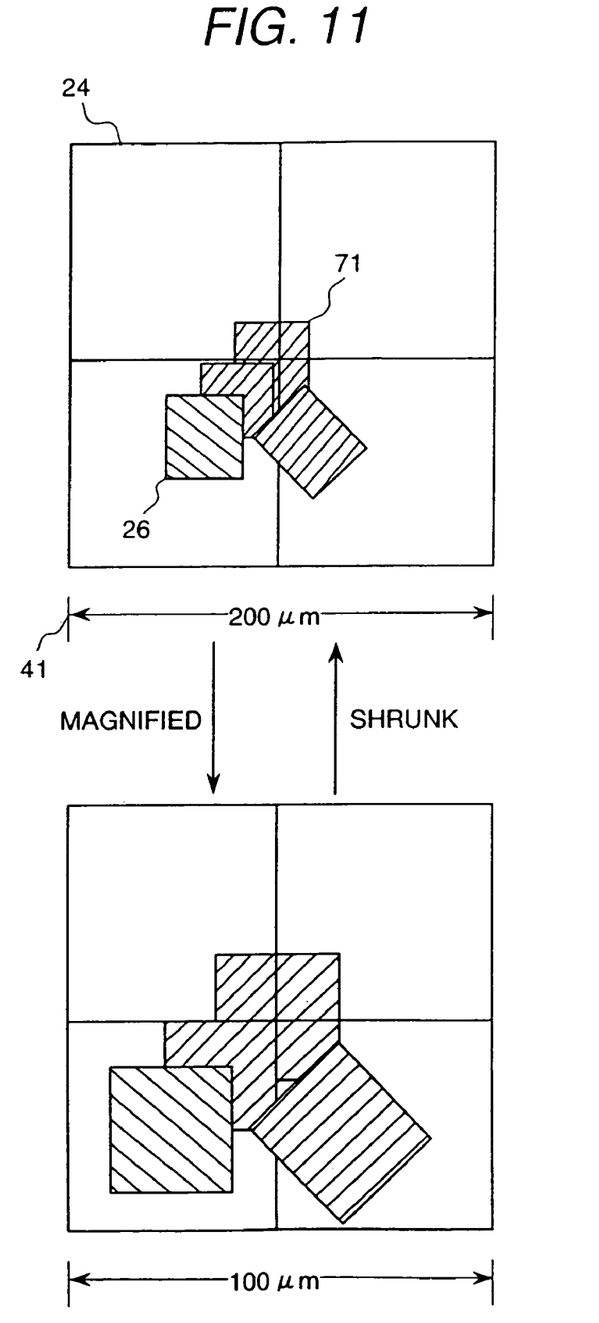
FIG. 11 shows an example of separately displaying areas, which are already observed and areas, which have not been observed in Embodiment 6.

FIG. 11 shows an example of separately displaying areas which are already observed and areas which have not been observed yet in accordance with the present invention.

The field-of-view 26 moves in the vicinity field 24 as the field of view of the electron microscope moves. In this case, the areas 71, which were already observed are displayed in different colors. This is also true when the field-of-view of the electron microscope is rotated.

Further, when the vicinity field including the field-of-view of the electron microscope is enlarged or shrunk, the areas 71 which were already observed are enlarged or shrunk according to the size of the vicinity field.

This prevents re-observation of the already-observed areas or skipping of observation of areas which have not been observed as the areas which were already observed are clearly distinguished from areas which have not been observed even when the field-of-view of the electron microscope is moved or rotated or the vicinity field including the field-of-view is enlarged or shrunk.

The present invention can provide an electron microscope for reviewing faults, which are detected by an optical inspecting apparatus, wherein said electron microscope can position its field of view easily and accurately on a target fault regardless of positional errors between different kinds of microscopes.

The invention claimed is:

1. An electron microscope for observing a surface or inside of a semiconductor wafer or a mask for exposing a semiconductor pattern for faults and/or foreign objects, comprising:
a function of loading measurement data of coordinates of said faults and/or foreign objects which were observed by another wafer or mask inspecting apparatus, moving a field of view of the electron microscope to an area of coordinates of said fault and/or foreign object, and simultaneously displaying said coordinates of said faults and/or objects which were obtained by observing said semiconductor wafer or said mask with said another wafer or mask inspecting apparatus, an electron microscope image of said field of view of the electron microscope, a vicinity area of said field of view of the electron microscope, showing said fault positions and sizes according to the coordinates and the sizes of said fault and/or foreign object observed by said another wafer or mask inspecting apparatus,
a function of moving said field of view of the electron microscope when the fault is not found to a position which is pointed by a pointer on a display, and
a function of magnifying said vicinity area after moving said field of view of the electron microscope,
wherein said field of view and the magnification of said vicinity area are automatically shrunk when said field of view of the electron microscope is not found in the vicinity area after the movement of the field of view of the electron microscope or said field of view and the magnification of the vicinity area are automatically enlarged when said field of view of the electron microscope is in the vicinity area after the movement of the field of view of the electron microscope.

2. An electron microscope in accordance with claim 1, further comprising a function which moves and displays the center coordinates of the field of view and its vicinity area as said field of view moves.

3. An electron microscope in accordance with claim 1, wherein said loaded measurement data further includes sizes of said faults and/or foreign objects and said display displays shapes of faults and/or foreign objects on a screen.

4. An electron microscope in accordance with claim 1, further comprising a function which displays coordinates of faults or objects obtained by said another wafer or mask inspecting apparatus and distances of the field of view of the electron microscope, a function which stores said distance values, and a function which relatively moves the field of view of the electron microscope by said stored distances.

5. An electron microscope in accordance with claim 1, further comprising a function which displays an observed area and a non-observed area separately on a screen displaying said field of view and its vicinity area, and a function which changes said display as the observing conditions of the electron microscope change.

6. An electron microscope for observing a surface or inside of a semiconductor wafer or a mask for exposing a semiconductor pattern for faults and/or foreign objects, comprising:
a memory device for storing coordinate information of sizes of said faults or foreign objects which were obtained by another wafer or mask inspecting apparatus,
a control computer for controlling so as to move a field of view of said the electron microscope to an area where a fault of foreign object exists based on said coordinate information, and
a display for simultaneously displaying said coordinates of said faults or objects which were obtained by observing said semiconductor wafer or said mask with said another wafer or mask inspecting apparatus, said field of view of said electron microscope moved according to the coordinates of said faults or objects which were obtained by another wafer or mask inspecting apparatus, and a vicinity area of said field of view of the electron microscope showing fault positions and sizes according to said coordinate information or sizes of said faults or foreign objects stored in said memory device,
a pointing device which moves said area indicating said field of view of said electron microscope to a position on said vicinity area which is pointed by the pointing device, wherein
said control computer controls said electron microscope so as to move said field of view of said electron microscope to said position on said vicinity area which is pointed to by said pointing device and calculates a magnification of displaying size of said field of view of said electron microscope and said vicinity area, and said display displays said semiconductor wafer or a mask observed in said field of view to said position on said vicinity area which is pointed to by the said pointing device and with the calculated magnification by the control computer, and wherein said field of view and the magnification of said vicinity area are automatically shrunk when said field of view of the electron microscope is not found in the vicinity area after the movement of the field of view of the electron microscope or said field of view and the magnification of the vicinity area are automatically enlarged when said field of view of the electron microscope is in the vicinity area after the movement of the field of view of the electron microscope.

7. An electron microscope in accordance with claim 6, wherein said display further displays a step value on a display to change an actual size of said vicinity area.

* * * * *

UNITED STATES PATENT AND TRADEMARK OFFICE
CERTIFICATE OF CORRECTION

PATENT NO.         : 7,214,937 B2                                    Page 1 of 1
APPLICATION NO. : 11/052809
DATED                  : May 8, 2007
INVENTOR(S)        : Katsuaki Abe et al.

It is certified that error appears in the above-identified patent and that said Letters Patent is hereby corrected as shown below:

<u>In the Title Page:</u>  After the listing of the inventors and before "(*) Notice:" change the assignee information to read as follows:

Item --(73) Assignee: Hitachi, Ltd., Tokyo (JP); and Hitachi Science Systems, Ltd., Ibaraki (JP)--

| <u>Column</u> | <u>Line</u> | |
|---|---|---|
| 3 | 62 | Change "defector" to --deflector-- |
| 4 | 1 | Change "AID-converted" to --A/D-converted--. |
| 6 | 64 | Change "field of view" to --field-of-view--. |
| 7 | 33 | After "coordinates" change "is" to --are--. |
| 8 | 7 | After "(e.g." insert --,--. |

Signed and Sealed this

Thirteenth Day of January, 2009

JON W. DUDAS
*Director of the United States Patent and Trademark Office*